US00PP17406P3

(12) United States Plant Patent
Gossett

(10) Patent No.: US PP17,406 P3
(45) Date of Patent: Feb. 13, 2007

(54) *SEDUM* PLANT NAMED 'CLOUD WALKER'

(50) Latin Name: ***Sedum* hybrid *(S. spectabile 'Brilliant'×S. telephium)***
Varietal Denomination: Cloud Walker

(75) Inventor: Gary J. Gossett, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 135 days.

(21) Appl. No.: 11/082,044

(22) Filed: Mar. 15, 2005

(65) Prior Publication Data

US 2006/0212983 P1 Sep. 21, 2006

(51) Int. Cl.
*A01H 5/00* (2006.01)

(52) U.S. Cl. ..... Plt./263

(58) Field of Classification Search ..... None
See application file for complete search history.

(56) References Cited

U.S. PATENT DOCUMENTS

PP15,582 P3 * 2/2005 Casertano ..... Plt./263

* cited by examiner

*Primary Examiner*—Wendy Haas
(74) *Attorney, Agent, or Firm*—Klarquist Sparkman, LLP

(57) ABSTRACT

A new and distinct hybrid of *Sedum* plant characterized by maroon tinted foliage and stems, large mauve colored flowers, and an open habit.

1 Drawing Sheet

Botanical denomination: *Sedum* hybrid (*S. spectabile* 'Brilliant'×*S. telephium*).

Variety designation: 'Cloud Walker'.

The present invention relates to a new and distinct cultivar of *Sedum* hybrid. and given the cultivar name of 'Cloud Walker'. *Sedum* is in the family Crassulaceae. *Sedum* 'Cloud Walker' originated from an open pollinated cross between *Sedum spectabile* 'Brilliant', an unpatented plant, as the seed parent, and an unknown dark leaf *Sedum telephium* as the pollen parent.

This new and unique *Sedum* is distinguished by:

1. Large mauve flowers.
2. Maroon tinted stems and foliage.
3. V-shaped, open habit of growth.
4. Short stature.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The photograph shows *Sedum* 'Cloud Walker' growing in the ground in August in the trial fields in Canby, Oreg.

DETAILED PLANT DESCRIPTION

The following is a detailed description of the new *Sedum* hybrid based on observations of one and a half year old specimen in September grown in the ground in full sun under typical outdoor conditions in the trial fields in Canby, Oreg. Canby is Zone 8 on the USDA Hardiness map. Temperatures range from a high of 95 degrees F. in August to an average low of 32 degrees F. in January. Normal rainfall in Canby is 42.8 inches per year. The color descriptions are all based on The Royal Horticultural Society Colour Chart.

Botanical denomination: *Sedum* hybrid (*S. spectabile* 'Brilliant'×*S. telephium*).

Variety designation: 'Cloud Walker'.

Plant:

*Type.*—Herbaceous perennial.
*Hardiness.*—USDA Zone 4 to 9.
*Size.*—34 cm tall from the ground to the top of the foliage and 70 cm wide.
*Habit.*—Spreading, V-shaped.
*Vigor.*—Excellent.
*Root description.*—Multiple fleshy roots from each crown, Yellow White 158A, grows to 5 mm wide and 20 cm long in clay loam soil.

Stem:

*Height.*—21 cm.
*Width.*—4 to 8 mm.
*Color.*—Yellow Green 145A at the base to Greyed Orange 174A with tints of Greyed Purple 184B.
*Texture.*—Succulent.
*Surface.*—Glaucous.

Leaf:

*Type.*—Simple.
*Arrangement.*—Opposite.
*Shape.*—Elliptic to slightly obovate.
*Venation.*—Pinnate.
*Margins.*—Coarsely and irregularly serrate.

*Apex.*—Broadly acute.
*Base.*—Cuneate.
*Blade size.*—Grows to 8 cm long and 4.3 cm wide.
*Surface.*—Glaucous.
*Texture.*—Thick, spongy, succulent.
*Petiole.*—Leaves sessile.
*Leaf color.*—Topside — Olive green (Yellow Green147A) suffused or tinged with grayed purple (Greyed Purple 187A). The color is variable depending on light and stress conditions. Leaves are darkest in full sun and low water. Bottom side — Green 138 B suffused or tinged with Greyed Green 194A.

Inflorescence:
*Type.*—Terminal, corymbose, umbel-like.
*Size.*—19 cm wide and 13 cm deep.
*Number of flowers.*—100 to 250 per branch, 6 branches.
*Peduncle.*—Height — 15 cm. Diameter — 7 cm. Color — Greyed Orange 177A and Greyed Purple 186A. Texture — Succulent. Surface — Glaucous.
*Bloom period.*—August through September in Canby, Oreg.
*Fragrance.*—None.
*Lastingness.*—Each corymb lasts about five weeks.

Flower bud:
*Size.*—3 mm wide, 8 mm deep.
*Description.*—Ovoid.
*Color.*—Greyed Purple 186C.

Flower:
*Type.*—Complete, actinomorphic.
*Shape.*—Stellate.
*Size.*—7 mm deep and 14 mm wide.
*Petal count.*—5.
*Petal color.*—Mauve, closest to Greyed Purple 186C but brighter pink.
*Petal shape.*—Lorate, reflex.
*Petal size.*—8 mm long, 1.5 mm wide.
*Calyx.*—Divided 4/5 to the base, campanulate, 3 mm deep and 2.5 mm wide.
*Calyx color.*—Greyed Orange 165A.
*Sepal number.*—5 lobes.
*Stamen number.*—5.
*Carpel.*—Prominent, 5 separate.
*Pistil size.*—6 mm deep and 1 mm wide.
*Pistil color.*—Greyed Purple 186A.
*Stamens.*—10, Greyed Purple 186A.
*Pollen color.*—No pollen, male sterile.

Fruit:
*Type.*—Capsule.
*Fertility.*—Very low, no seed formed.
*Color.*—Tan, closest to Greyed Brown 199A.

Seed: No seed formed, sterile.

Pests and diseases: *Sedum* are susceptible to mealy bugs, scale insects, slugs and snails. No problems have been noted for this variety. All *Sedum* will develop root rot in wet conditions.

COMPARISON TO SIMILAR *SEDUM*

Compared to *Sedum spectabile* 'Brilliant', an unpatented plant similar and analogous to the mother parent, *Sedum* 'Cloud Walker' has darker foliage and stem and smaller inflorescences with duller pink flowers. The new variety is shorter, more branched and the habit is mounding and v-shaped rather than upright.

Compared to *Sedum* 'Ruby Glow', an unpatented plant, *Sedum* 'Cloud Walker' is more upright, taller, and has flowers that are larger on larger inflorescences. They have similar flower color.

I claim:

1. A new and distinct hybrid of *Sedum* plant as herein illustrated and described.

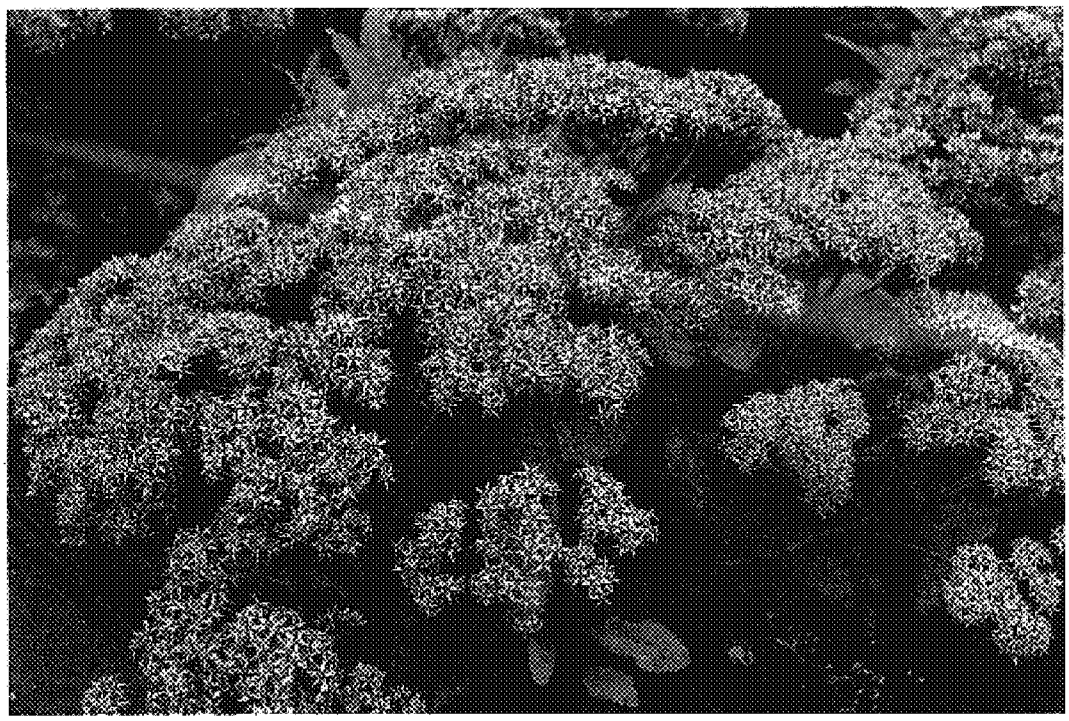

* * * * *